United States Patent [19]  
Martel et al.

[11] 4,166,063  
[45] Aug. 28, 1979

[54] LACTONES OF 2,2-DIMETHYL-CYCLOPROPANE-1-CARBOXYLIC ACIDS

[75] Inventors: Jacques Martel, Bondy; Jean Tessier, Vincennes; Jean-Pierre Demoute, Montreuil-sous-Bois; Jean Jolly, Fontenay-sous-Bois, all of France

[73] Assignee: Roussel Uclaf, Paris, France

[21] Appl. No.: 914,399

[22] Filed: Jun. 12, 1978

[30] Foreign Application Priority Data

Jun. 27, 1977 [FR] France ................. 77 19612

[51] Int. Cl.² .......................... C07D 307/93
[52] U.S. Cl. ................ 260/343.3 R; 562/506
[58] Field of Search .................. 260/343.3 R

[56] References Cited
U.S. PATENT DOCUMENTS 3,723,469  3/1973  Martel .............. 260/343.3 R

FOREIGN PATENT DOCUMENTS 2185612  5/1973  France .
51-122041  10/1976  Japan .

OTHER PUBLICATIONS

Servin et al., Tetrahedron Letters, No. 43, pp. 3915-3918, 1976.
Martel, Chem. Abstracts, vol. 72, 1970, 100136d, 121078b.

Primary Examiner—Natalie Trousof  
Assistant Examiner—Jane T. Fan  
Attorney, Agent, or Firm—Hammond & Littell

[57] ABSTRACT

Novel lactones of 2,2-dimethyl-cyclopropane-1-carboxylic acids of the formula

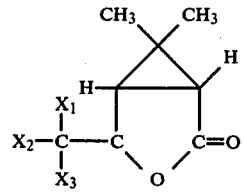

wherein $X_1$, $X_2$ and $X_3$ when identical are selected from the group consisting of chlorine and bromine and when at least two are different, are selected from the group consisting of fluorine, chlorine and bromine and a novel process for their preparation and a process for the preparation of cis 2,2-dimethyl-cyclopropane-1-carboxylic acids of the formula

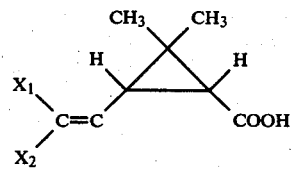

4 Claims, No Drawings

LACTONES OF 2,2-DIMETHYL-CYCLOPROPANE-1-CARBOXYLIC ACIDS

STATE OF THE ART

French Pat. No. 2,185,612 describes a process from the production of cis 2,2-dimethyl-cyclopropane-1-carboxylic acids of formula IV by reacting triphenylphosphine with a haloform and an aldehyde ester of the formula

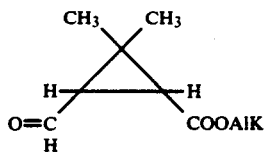

wherein alkyl is a lower alkyl. The process proceeds by the triphenylphosphine and the haloform reacting to obtain diverse condensation products including the intermediate

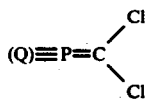

which then reacts with the carbonyl of the aldehyde to form the acid of formula IV [Appel, et al, Chem. Ber., Vol. 58 (1976) p. 70 and French Pat. No. 2,185,612, p. 15, lines 15 to 27].

OBJECTS OF THE INVENTION

It is an object of the invention to provide the novel lactones of formula I and a novel process for their preparation.

It is another object of the invention to provide a novel process for the preparation of cis cyclopropane-1-carboxylic acids of formula IV.

These and other objects and advantages of the invention will become obvious from the following detailed description.

THE INVENTION

The novel compounds of the invention are lactones of 2,2-dimethyl-cyclopropane-1-carboxylic acids of the formula

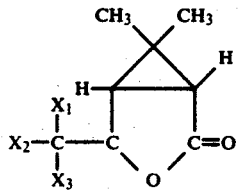

wherein $X_1$, $X_2$ and $X_3$ when identical are selected from the group consisting of chlorine and bromine and when two are different, are selected from the group consisting of fluorine, chlorine and bromine.

Examples of preferred specific compounds of formula I are the lactone of 1R, cis 2,2-dimethyl-3-(1'-hydroxy-2',2',2'-trichloroethyl)-cyclopropane-1-carboxylic acid, the lactone of 1R, cis 2,2-dimethyl-3-(1'-hydroxy-2',2',2'-tribromoethyl)-cyclopropane-1-carboxylic acid and the lactone of 1R, cis 2,2-dimethyl-3-(1'-hydroxy-2'-fluoro-2', 2'-dichloroethyl)-cyclopropane-1-carboxylic acid.

The novel process of the invention for the preparation of compounds of formula I comprises reacting in the presence of a basic agent a compound of the formula

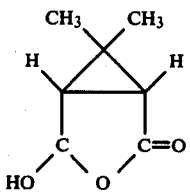

with a haloform of the formula

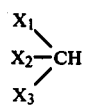

wherein $X_1$, $X_2$ and $X_3$ have the above definition to obtain a compound of the formula

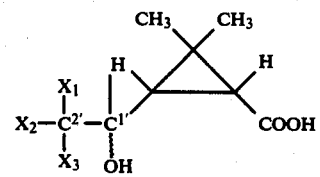

and reacting the latter with an acid agent or a deshydrating agent or subjecting the latter to heat to obtain the corresponding compound of formula I.

The process is illustrated by the following reaction scheme

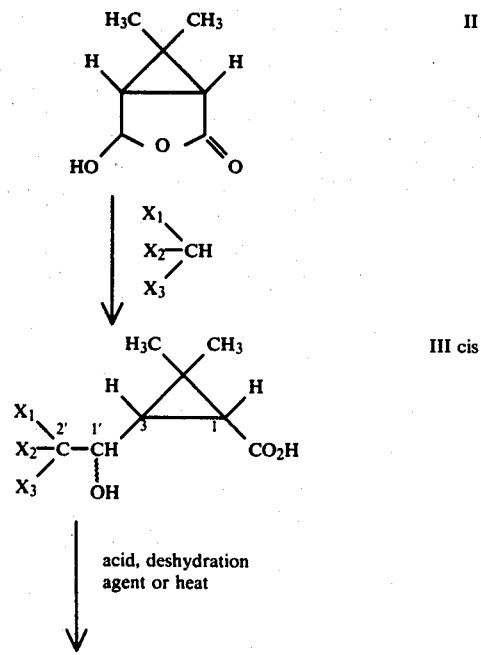

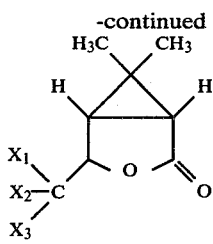

The intermediate compounds of formula III have 2 asymetrical centers in the 1 and 3 position of the cyclopropane ring and possess an asymetrical carbon in the 1'-position of the ethylene side chain. The diastereisomers of the 1'-carbon atom of the side chain are named the A and B isomers. Without going into the theoretical considerations, with the compounds of formula III in the cis form, the A isomer is the structure 1'S and the B isomer is the structure 1'R.

When $X_1$, $X_2$ and $X_3$ are different from each other, the compounds of formula III contain an asymetrical carbon in the 2'-position of the ethylene side chain which causes the existence of a supplementary category of stereoisomers.

In a preferred embodiment, the basic agent for the condensation step is selected from the group consisting of alkali metal alcoholates, alkali metal hydrides and alkali metal hydroxides and the condensation is preferably effected in one or more organic solvents selected from the group consisting of alkanols, dimethylformamide, dimethylsulfoxide, tetrahydrofuran, hexamethylphosphorotriamide, ether oxides and aliphatic hydrocarbons.

Especially preferred is the use of potassium tert.-butylate in a mixture of tert.-butanol and tetrahydrofuran or a mixture of tert.-butanol, tetrahydrofuran and hexamethylphosphorotriamide. The use of potassium methylate is also useful and the preferred solvent system is a mixture of dimethylformamide and tetrahydrofuran or a mixture of tert.-butanol, dimethylformamide and tetrahydrofuran. Also useful as the basic agent is potassium hydroxide in a mixture of methanol and tetrahydrofuran.

The acid agent for reaction with the compound of formula III is preferably selected from the group consisting of p-toluene sulfonic acid, sulfuric acid, acetic acid, acetic acid anhydride and a mixture of acetic acid and its anhydride. The preferred acid agent is p-toluene sulfonic acid and the process is operated at reflux in a solvent such as benzene or toluene while azeotropically distilling off the water of reaction.

The deshydration agent for reaction with the compounds of formula III is preferably selected from the group consisting of phosphoric anhydride and dicyclohexylcarbodiimide. The compounds of formula III may also be converted to compounds of formula I by heating for a few minutes to obtain practically quantitative yields of compounds of formula I.

The process of the invention for the preparation of cis compounds of formula IV comprises reacting a compound of formula I with a reducing agent to eliminate the $X_3$ substituent which is the halogen with the higher atomic number to obtain the corresponding compound of formula IV. The reducing agent is preferably selected from the group consisting of zinc in the presence of acetic acid, magnesium or a zinc-copper couple in a lower alkanol. The reaction is illustrated as follows:

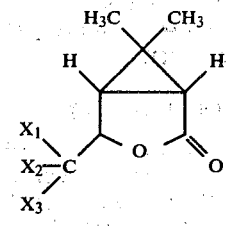

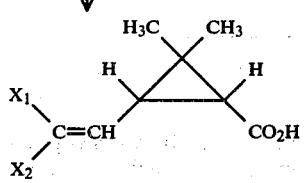

The starting compounds of formula II are easily prepared such as described in French Pat. No. 1,580,474.

The compounds of formula I are of great industrial importance as they permit the preparation in a single step using readily accessible reactants of the cis cyclopropane-1-carboxylic acids of formula IV which can be directly esterified or converted into a functional derivative and esterified with an alcohol which esters are known to have extremely high insecticidal activity (French Pat. Nos. 2,185,612 and 2,240,914).

The mechanism of the reaction leading to the formation of compounds of formula IV is fundamentally different from the process of French Pat. No. 2,185,612 as it consists of fixing a haloform in a basic media to the lactone of formula II to form the compounds of formula III which after lactonization to form the compounds of formula I, the group

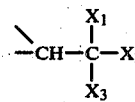

may then be reduced to form the dihalovinyl side chain of the compounds of formula IV.

It should be noted that the obtention of high yields in the reduction of compounds of formula I to compounds of formula IV is unexpected since, a priori, it could be expected two halogens and not one would be removed resulting in an undesired monohalogenated product and to a lower yield of the compounds of formula IV. Finally, the series of reactions permit access of compounds of formula IV and is more advantageous and more economical than the process of French Pat. No. 2,185,612.

The reactions of the present invention use reactants which are less costly and readily accessible as compared to triphenylphosphine which is a burdensome reactant. Moreover, the yields of the reactions of the processes of the invention are high and therefore, the total yield going from compounds of formula II to compounds of formula IV are higher than the yields of the process of the above French patent. In effect, the reaction of triphenylphosphine with the haloform to form the desired intermediate

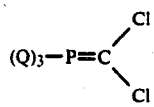

is accompanied by formation of substantial amounts of diverse secondary products which will not react with the carbonyl aldehyde to form the dihalovinyl carboxylic acids of formula IV.

Japanese patent application Ser. No. 46247/1975 describes the formation of compounds with a dihalovinyl chain but the steps described therein are more numerous than the steps of the present invention and lead to compounds with the trans structure rather than the cis structure and it is impossible to form the lactones of formula I. The cis compounds of the present invention permit the preparation of insecticidal esters with a higher activity than the trans esters produced by the Japanese application.

The process of the invention has an unexpected chemical plan since in effect it would be expected that in a basic media the compounds of formula II would at least partially epimerize into the tautomeric compounds of the trans structure. It would be expected, a priori, that the addition of the haloform in a basic media would lead to such an epimerization leading to the undesirable trans compounds. However, it has been found that the process of the invention does not lead to such an epimerization, probably because the rate of addition of haloform is greater than the rate of epimerization of the cis derivatives to the trans derivative. The retention of the desired cis configuration observed could not be predicted a priori and contains for the processes of the invention an unexpected character.

In the following examples there are described several preferred embodiments to illustrate the invention. However, it is to be understood that the invention is not intended to be limited to the specific embodiments.

EXAMPLE 1

1R, cis 2,2-dimethyl-3-(1'-hydroxy-2',2',2'-trichloroethyl)-cyclopropane-1-carboxylic acid 2.84 g of the lactone of 2,2-dimethyl-3S-formylcyclopropane-1R-carboxylic acid with a specific rotation of $[\alpha]_D^{20} = -110°$ (c=1.0% in dimethylformamide) were added to a mixture of 30 ml of dimethylformamide and 10 ml of chloroform and then a solution of 4.5 g of potassium tert.-butylate in a mixture of 20 ml of tert.-butanol and 10 ml of tetrahydrofuran was added thereto dropwise at $-50°$ C. The reaction mixture was stirred at $-50°$ C. for 30 minutes and was then poured into an aqueous monosodium phosphate solution. The mixture was extracted with benzene and the benzene extracts were washed with water, dried and concentrated to dryness under reduced pressure. The residue was added to water and the mixture was vacuum filtered. The crystals were dried to obtain 5 g of 1R, cis 2,2-dimethyl-3-(1'hydroxy-2,',2',2'-trichloroethyl)-cyclopropane-1-carboxylic acid melting at 182° C.

I.R. Spectrum (chloroform):
Absorption at 1690 cm$^{-1}$; 1725 cm$^{-1}$ (shoulder); 3500 cm$^{-1}$; and 3575 cm$^{-1}$ RMN Spectrum: B isomer
Peaks at 1.25–1.32 ppm (hydrogens of 2-methyls of cyclopropane); at 1.32 to 1.82 ppm (1- and 3-hydrogens of cyclopropane); at 4.35 and 4.50 ppm (1'-hydrogen of 3-ethyl chain of cyclopropane).

EXAMPLE 2

1R, cis 2,2-dimethyl-3-(1'-hydroxy-2',2',2'-tribromoethyl)-cyclopropane-1-carboxylic acid 2.84 g of the lactone of 2,2-dimethyl-3S-formyl-cyclopropane-1R-carboxylic acid with a specific rotation of $[\alpha]_D^{20} = -110°$ (c=1% in dimethylformamide) were added to a mixture of 30 ml of dimethylformamide and 5 ml of bromoform and then a solution of 4.5 g of potassium tert.-butylate in 20 ml of tert.-butanol and 10 ml of tetrahydrofuran was added dropwise thereto at $-50°$ C. The mixture was stirred at $-50°$ C. for 15 minutes and was then poured into an aqueous monosodium phosphate solution. The mixture was extracted with methylene chloride and the organic extracts were washed with water, dried and evaporated to dryness under reduced pressure. The residue was added to an aqueous sodium bicarbonate solution and was stirred and filtered. The aqueous filtrate was washed with methylene chloride to remove non-acidic impurities and was acidified to a pH of 1 with 10 N hydrochloric acid. The mixture was vacuum filtered and the recovered precipitate was washed and dried to obtain 5.9 g of 1R, cis 2,2-dimethyl-3-(1'-hydroxy-2',2',2'-tribromoethyl)-cyclopropane-1-carboxylic acid melting at 120° C. and then 177° C. (contained solvated water).

I.R. Spectrum (chloroform):
Absorption at 1691 cm$^{-1}$; 3560–3570 cm$^{-1}$

RMN Spectrum: B isomer
Peaks at 1.27–1.37 ppm (hydrogens of 2-methyls of cyclopropane); 1.37 to 1.78 ppm (1- and 3-hydrogens of cyclopropane); 4.1–4.25 ppm (hydrogen α to tribromomethyl); 6.08 ppm (hydrogen of hydroxy α to tribromomethyl).

EXAMPLE 3

1R, cis 2,2-dimethyl-3-(1'-hydroxy-2',2',2'-tribromoethyl)-cyclopropane-1-carboxylic acid 18.5 ml of bromoform were added to a mixture of 20 g of the lactone of 2,2-dimethyl-3S-formyl-cyclopropane-1R-carboxylic acid in 100 ml of tetrahydrofuran and then a solution of 18 g of potassium tert.-butylate in a mixture of 70 ml of tert.-butanol and 70 ml of tetrahydrofuran were slowly added thereto at $-10°$ C. The mixture was stirred at $-10°$ C. for 30 minutes and water was added with stirring. The aqueous phase was extracted with methylene chloride and was acidified to a pH of 1 with aqueous hydrochloric acid. The mixture was vacuum filtered and the recovered product was washed with water and dried to obtain 48.4 g of 1R, cis 2,2-dimethyl-3-(1'-hydroxy-2',2',2'-tribromoethyl)-cyclopropane-1-carboxylic acid melting at 120° C. and then 177° C.

EXAMPLE 4

1R, cis 2,2-dimethyl-3-(1'-hydroxy-2',2',2'-tribromoethyl)-cyclopropane-1-carboxylic acid 18.5 ml of bromoform were added at $-10°$ C. to a mixture of 20 g of the lactone of 2,2-dimethyl-3S-formylcyclopropane-1R-carboxylic acid in 100 ml of tetrahydrofuran and then a solution of 11.2 g of potassium methylate in 50 ml of tert.-butanol, 10 ml of dimethylformamide and 30 ml of tetrahydrofuran was slowly added thereto at −10° C. The mixture was stirred at −10° C. for 30 minutes and was treated as in Example 3 to obtain 51 g of 1R, cis 2,2-dimethyl-3-(1′-hydroxy-2′,2′,2′-tribromoethyl)-cyclopropane-1-carboxylic acid of the same quality as in Example 3.

EXAMPLE 5

1R, cis 2,2-dimethyl-3-(1′-hydroxy-2′,2′,2′-tribromoethyl)-cyclopropane-1-carboxylic acid 18.5 ml of bromoform were added at −10° C. to a mixture of 20 g of the lactone of 2,2-dimethyl-3S-formylcyclopropane-1R-carboxylic acid in 100 ml of tetrahydrofuran and then a mixture of 35 ml of a methanolic solution of potassium hydroxide (titrating 27 g/ml) and 30 ml of tetrahydrofuran was slowly added thereto at −10° C. The mixture was stirred at −10° C. for 90 minutes and was then treated as in Example 3 to obtain 43.3 g of 1R, cis 2,2-dimethyl-3-(1′-hydroxy-2′,2′,2′-tribromoethyl)-cyclopropane-1-carboxylic acid of the same quality as Example 3.

EXAMPLE 6

1R, cis 2,2-dimethyl-3-(1′-hydroxy-2′-fluoro-2′,2′-dichloroethyl)-cyclopropane-1-carboxylic acid 30 g of dichlorofluoromethane were added at −20° C. to a solution of 28.4 g of the lactone of 2,2-dimethyl-3S-formyl-cyclopropane-1R-carboxylic acid in 300 ml of dimethylformamide and then a mixture of 45 g of potassium tert.-butylate (95% titration) in 100 ml of tetrahydrofuran and 200 ml of tert.-butanol was added thereto over 30 minutes at −55° C. The mixture was stirred for 17 hours at −50° C. and then 2 hours at −20° C. and was then poured into a mixture of water, ice and hydrochloric acid. The mixture was extracted with benzene and the benzene extracts were evaporated to dryness to obtain 39 g of raw product which was chromatographed over silica gel. Elution with a 9-1 chloroform-methanol mixture yielded 1R, cis 2,2-dimethyl-3-(1′-hydroxy-2′-fluoro-2′,2′-dichloroethyl)-cyclopropane-1-carboxylic acid melting at 142° C.

Analysis: $C_8H_{11}Cl_2FO_3$; molecular weight=245.08
Calculated: %C 39.20; %H 4.52; %Cl 28.93; %F 7.75;
Found: 39.4; 4.6; 28.9; 8.0.
I.R. Spectrum (chloroform):
 Absorption at 3580 cm$^{-1}$ (alcoholic hydroxy); 3500 cm$^{-1}$ (—COOH); 1693 and 1725 cm$^{-1}$ (C=O).
RMN Spectrum (ducterochloroform):
 Peaks at 1.25–1.35 ppm (hydrogens of geminal methyls); 1.5–1.92 ppm (hydrogens of cyclopropyl); 4.37–4.52–4.65 ppm (1′-hydrogen of lateral ethyl chain).

EXAMPLE 7 lactone of 1R, cis 2,2-dimethyl-3-(1′-hydroxy-2′,2′,2′-tribromoethyl)-cyclopropane-1-carboxylic acid 3.94 g of 1R, cis 2,2-dimethyl-3-(1′-hydroxy-2′,2′,2′-tribromoethyl)-cyclopropane-1-carboxylic acid were added to a mixture of 11.8 ml of acetic acid and 3.94 ml of acetic acid anhydride and the mixture was heated at 80° C. for 4 hours and was then cooled to 20° C. The mixture was poured into water and was evaporated to dryness to obtain 3.63 g of the lactone of 1R, cis 2,2-dimethyl-3-(1′-hydroxy-2′,2′,2′-tribromoethyl)-cyclopropane-1-carboxylic acid melting at 94° C.

EXAMPLE 8 lactone of 1R, cis 2,2-dimethyl-3-(1′-hydroxy-2′,2′,2′-tribromoethyl)-cyclopropane-1-carboxylic acid A mixture of 3.94 g of 1R, cis 2,2-dimethyl-3-(1′-hydroxy-2′,2′,2′-tribromoethyl)-cyclopropane-1-carboxylic acid and 3.9 ml of 36 N sulfuric acid was stirred at 20° C. for 2 hours and was then poured into a mixture of ice and water. The mixture was extracted with methylene chloride and the organic extracts were washed with an aqueous 10% sodium bicarbonate solution, then with water and dried and evaporated to dryness to obtain 3.13 g of the lactone of 1R, cis 2,2-dimethyl-3-(1′-hydroxy-2′,2′,2′-tribromoethyl)-cyclopropane-1-carboxylic acid.

EXAMPLE 9 lactone of 1R, cis 2,2-dimethyl-3-(1′-hydroxy-2′,2′,2′-tribromoethyl)-cyclopropane-1-carboxylic acid A mixture of 3.94 g of 1R, cis 2,2-dimethyl-3-(1′-hydroxy-2′,2′,2′-tribromoethyl)-cyclopropane-1-carboxylic acid and 7.9 g of acetic acid anhydride was stirred at 85° C. for 1 hour and was then distilled to remove excess acetic acid anhydride to obtain 3.47 g of the lactone of 1R, cis 2,2-dimethyl-3-(1′-hydroxy-2′,2′,2′-tribromoethyl)-cyclopropane-1-carboxylic acid.

EXAMPLE 10 lactone of 1R, cis 2,2-dimethyl-3-(1′-hydroxy-2′,2′,2′-trichloroethyl)-cyclopropane-1-carboxylic acid A mixture of 7.84 g of the product of Example 1, 100 mg of p-toluene sulfonic acid and 78 ml of benzene was refluxed for one hour in a ballon flask provided with an apparatus of the Dean-Stark type for azeotropic distillation of water. The reaction mixture was cooled and was washed with an aqueous sodium bicarbonate solution, dried and evaporated to dryness under reduced pressure. The residue was empasted with pentane to obtain 6.50 g of the lactone of 1R, cis 2,2-dimethyl-3-(1′-hydroxy-2′,2′,2′-trichloroethyl)-cyclopropane-1-carboxylic acid melting at 75° C.
I.R. Spectrum (chloroform):
 Absorption at 1784 cm$^{-1}$
RMN Spectrum:
 Peaks at 1.25 ppm (hydrogens of 2-methyls of cyclopropane); 2.06–2.16–2.3–2.4 ppm (1- and 3-hydrogens of cyclopropane); 4.58 ppm (hydrogen α to trichloromethyl).

EXAMPLE 11 lactone of 1R, cis 2,2-dimethyl-3-(1′-hydroxy-2′,2′,2′-tribromoethyl)-cyclopropane-1-carboxylic acid A mixture of 100 ml of benzene, 5 g of the product of Example 2 and 150 mg of p-toluene sulfonic acid was refluxed for 1 hour in a ballon flask provided with a Dean-Stark type apparatus for azeotropic distillation of water and was then cooled. The mixture was washed with an aqueous sodium bicarbonate solution and with water, was dried and evaporated to dryness under reduced pressure to obtain 4.40 g of the lactone of 1R, cis 2,2-dimethyl-3-(1'-hydroxy-2',2',2'-tribromoethyl)-cyclopropane-1-carboxylic acid melting at 89° C. After crystallization from a mixture of isopropyl ether and essence G (b.p.=35°-75° C.), the product melted at 90° C.

I.R. Spectrum (chloroform):
Absorption at 1785 cm$^{-1}$ and 1805 cm$^{-1}$
RMN Spectrum:
Peaks at 1.26–1.28 ppm (hydrogens of 2-methyls of cyclopropane); at 2.08–2.18–2.27–2.36 ppm (1- and 3-hydrogens of cyclopropane); at 4.52 ppm (hydrogen α to tribromomethyl).

EXAMPLE 12 lactone of 1R, cis 2,2-dimethyl-3-(1'-hydroxy-2'-fluoro-2', 2'-dichloroethyl)-cyclopropane-1-carboxylic acid 0.5 g of p-toluene sulfonic acid was added to a solution of the raw product of Example 6 in 100 ml of benzene and the mixture was refluxed for 17 hours while removing water by azeotropic distillation. The mixture was cooled to 20° C. and the organic phase was washed with 1 N sodium hydroxide solution and then with water and was evaporated to dryness. The residue was chromatographed over silica gel and was eluted with benzene to obtain 21 g of the lactone of 1R, cis 2,2-dimethyl-3-(1'-hydroxy-2'-fluoro-2',2'-dichloroethyl)-cyclopropane-1-carboxylic acid melting at 64° C.
RMN Spectrum (deuterochloroform):
Peaks at 1.27 ppm (hydrogens of geminal methyls); at 2.07–2.17–2.23–2.33 ppm (hydrogens of cyclopropyl); at 4.53–4.66 ppm (hydrogens α to CCl$_2$F).

EXAMPLE 13

1R, cis 2,2-dimethyl-3-(2',2'-dichlorovinyl)-cyclopropane-1-carboxylic acid 10 g of powdered zinc were added at 20° C. to a mixture of 3.4 g of the lactone of 1R, cis 2,2-dimethyl-3-(1'-hydroxy-2',2',2'-trichloroethyl)-cyclopropane-1-carboxylic acid in 35 ml of acetic acid containing 10% of water and the mixture was stirred for one hour at 20° C. and was filtered to remove insolubles. The filtrate was extracted with methylene chloride and the organic extracts were washed with water, dried and evaporated to dryness under reduced pressure. The residue was added to 1N sodium hydroxide solution and the aqueous phase was extracted with methylene chloride to remove non-acidic impurities. The pH of the aqueous phase was adjusted to 1 and was vacuum filtered. The recovered precipitate was washed with water and dried to obtain 2.30 g of 1R, cis 2,2-dimethyl-3-(2',2'-dichlorovinyl)-cyclopropane-1-carboxylic acid melting at 92° C. and having a specific rotation of $[\alpha]_D^{20} = +31.5°$ (c=1% in dimethylformamide).

EXAMPLE 14

1R, cis 2,2-dimethyl-3-(2',2'-dibromovinyl)-cyclopropane-1-carboxylic acid

Using the procedure of Example 13, 3.58 g of the lactone of 1R, cis 2,2-dimethyl-3-(1'-hydroxy-2',2',2'-tribromoethyl)-cyclopropane-1-carboxylic acid were reacted to obtain 2.16 g of 1R, cis 2,2-dimethyl-3-(2',2'-dibromovinyl)-cyclopropane-1-carboxylic acid melting at 129° C.

EXAMPLE 15

1R, cis 2,2-dimethyl-3-(2',2'-dibromovinyl)-cyclopropane-1-carboxylic acid 1 g of magnesium turnings were placed in a vessel under a nitrogen atmosphere and then 10% of a solution of 10 g of the lactone of 1R, cis 2,2-dimethyl-3-(1'-hydroxy-2',2',2'-tribromoethyl)-cyclopropane-1-carboxylic acid in 50 ml of tetrahydrofuran were added thereto at 20° C. A small amount of iodine was added to start the reaction and then the remaining 90% of the solution was added thereto over 20 minutes at 30° to 35° C. The mixture was stirred under nitrogen at 20° C. for 16 hours and was then vacuum filtered to remove insolubles. The filtrate was evaporated to a volume of about 20 ml and aqueous ammonium chloride solution was added thereto. The pH of the mixture was adjusted to 1 by addition of a concentrated aqueous hydrochloric acid solution and was extracted with methylene chloride. The organic extracts were washed with water and with aqueous N sodium hydroxide solution. The aqueous alkaline phase was extracted with methylene chloride and animal black was added to the aqueous phase which was then stirred and filtered. The filtrate was adjusted to a pH of 1 with concentrated aqueous hydrochloric acid. The mixture was vacuum filtered and the recovered precipitate was washed and dried and crystallized from a 1-1 acetic acid-water mixture to obtain 4.3 g of 1R, cis 2,2-dimethyl-3-(2', 2'-dibromovinyl)-cyclopropane-1-carboxylic acid.

EXAMPLE 16

1R, cis 2,2-dimethyl-3-(2'-chloro-2'-fluorovinyl)-cyclopropane-1-carboxylic acid 1.5 ml of aqueous 22° Be hydrochloric acid solution was added with brief stirring to a refluxing mixture of 12 g of zinc and 50 ml of ethanol and the mixture was stirred one minute and was vacuum filtered hot. The zinc was washed several times with ethanol to obtain active zinc. All the active zinc was then added to a solution of 6 g of the lactone of Example 12 and the mixture was refluxed with stirring for 3 hours. The mixture was filtered and the filter was washed with ethanol and chloroform. The combined filtrates were evaporated to dryness under reduced pressure and the residue was added to chloroform. The resulting solution was washed with N aqueous hydrochloric acid, with water and was extracted with 1N aqueous sodium hydroxide solution. The aqueous alkaline phase was washed with chloroform and was then acidified to a pH of 1. The mixture was extracted with chloroform and the organic extracts were washed with water and evaporated to dryness to obtain 4.5 g of a mixture of E and Z isomers of 1R, cis 2,2-dimethyl-3-(2'-chloro-2'-fluorovinyl)-cyclopropane-1-carboxylic acid.
RMN Spectrum (deuterochloroform):
Peaks at 1.28 ppm (hydrogens of geminal methyls); 5.03–5.20–5.53–5.68 ppm (ethylenic hydrogen—E isomer); at 5.5–6.03 ppm (ethylenic hydrogen—Z isomer); at 11.4 ppm (hydrogen of carboxyl); at 1.67–2.33 ppm (hydrogens of cyclopropyl).

Various modifications of the products and processes of the invention may be made without departing from the spirit or scope thereof and it is to be understood that the invention is intended to be limited only as defined in the appended claims.

We claim:

1. A lactone of a 2,2-dimethyl-cyclopropane-1-carboxylic acid of the formula

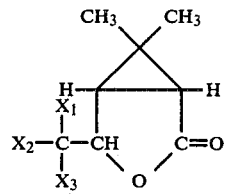

wherein $X_1$, $X_2$ and $X_3$ when identical are selected from the group consisting of chlorine and bromine and when at least two are different, are selected from the group consisting of fluorine, chlorine and bromine.

2. A compound of claim 1 which is the lactone of 1R, cis 2,2-dimethyl-3-(1'-hydroxy-2',2',2'-trichloroethyl)-cyclopropane-1-carboxylic acid.

3. A compound of claim 1 which is the lactone of 1R, cis 2,2-dimethyl-3-(1'-hydroxy-2',2',2'-tribromoethyl)-cyclopropane-1-carboxylic acid.

4. A compound of claim 1 which is the lactone of 1R, cis 2,2-dimethyl-3-(1-hydroxy2'-fluoro-2',2'-dichloroethyl)-cyclopropane-1-carboxylic acid.

* * * * *